(12) United States Patent
Myasoedov et al.

(10) Patent No.: US 8,883,741 B2
(45) Date of Patent: Nov. 11, 2014

(54) STIMULATOR OF GENITAL, SEXUAL AND REPRODUCTIVE FUNCTION

(75) Inventors: Nikolay Fedorovich Myasoedov, Moscow (RU); Alim Vasilievich Nemersky, Moscow (RU); Mikhail Alexandrovich Mogutov, Moscow (RU); Tatiyana Nikolaevna Sollertinskaya, Saint Petersburg (RU); Mstislav Vladilenovich Shoroshov, Saint Petersburg (RU); Dmitry Viktorovich Golikov, Moscow (RU)

(73) Assignee: Bio Peptid Company Limited, Moscow (RU)

( * ) Notice: Subject to any disclaimer, the term of this patent is extended or adjusted under 35 U.S.C. 154(b) by 203 days.

(21) Appl. No.: 13/376,023

(22) PCT Filed: Jun. 1, 2010

(86) PCT No.: PCT/RU2010/000285
§ 371 (c)(1),
(2), (4) Date: Feb. 2, 2012

(87) PCT Pub. No.: WO2010/140926
PCT Pub. Date: Dec. 9, 2010

(65) Prior Publication Data
US 2012/0129791 A1  May 24, 2012

(30) Foreign Application Priority Data
Jun. 4, 2009  (RU) .................. 2009121281

(51) Int. Cl.
A61K 38/08  (2006.01)
(52) U.S. Cl.
CPC ...................... A61K 38/08 (2013.01)
USPC ....................................... 514/21.7
(58) Field of Classification Search
CPC ............... A61K 38/18; A61K 38/00
See application file for complete search history.

(56) References Cited

U.S. PATENT DOCUMENTS

| 5,932,548 A | 8/1999 | Deghenghi |
| 5,955,421 A | 9/1999 | Deghenghi |
| 6,211,156 B1 | 4/2001 | Argiolas et al. |

FOREIGN PATENT DOCUMENTS

| CN | 101302246 | 11/2008 |
| CN | 101302246 A | 11/2008 |
| EA | 013948 | 8/2010 |
| RU | 1124544 | 1/1995 |
| RU | 2058791 | 4/1996 |
| RU | 2155065 | 8/2000 |
| RU | 2252779 | 5/2005 |
| RU | 2264823 | 11/2005 |
| RU | 2290195 | 12/2006 |
| RU | 2404793 | 11/2010 |
| WO | WO 94/22460 | 10/1994 |
| WO | WO 01/34171 | 5/2001 |

OTHER PUBLICATIONS

Ashmarin et al., "Natural and hybrid ("chimeric") stable regulatory glyproline peptide", Pathophysiology, 2005, pp. 179-185.*
Sollertinskaya et al., "Compensatory and Antiamnestic Effects of Heptapeptide Selank in Monkeys", Journal of Evolutionary Biochemistry and Physiology, 2008, pp. 332-340.*
Kumar et al., "Sexual Behavior in Normal and Neurotic Females", Indian J. Psychiat., 1984, pp. 213-218.*
Diamond, et al., Co-administration of low doses of intranasal PT-141, a melanocortin receptor agonist, and sildenafil to men with erectile dysfunction results in an enhanced erectile response, Urology, vol. 65, No. 4, pp. 755-759, 2005.
Extended European Search Report for European Patent Application No. 10783644.7, dated Nov. 15, 2012.
English-language abstract of Chinese Patent Publication No. CN101302246; Database WPI, Week 200912, Thompson Scientific, London, GB; AN 2009-B41118 XP002686138, & CN 101 302 246 A (Inst Toxicant & Medicament Acad Military) Nov. 12, 2008 Abstract.
Kozlovskaya et al, Comparison study of series of tuftsin's fragments of short-time and durable action on the index of conditional reactions of passive avoidance, Chimiko-pharmac. Zh. 35 (2001) 3-5.
Kozlovskaya et al, Selank and short peptides of Tuftsin derivatives in regulation of adaptive behaviour of animal in stress, Ross. Fiziol. Zh. Im. I. M. Sechenova. 88 (2002) 751-761.
Seredinin et al., The Study of Anxiolytic Activity of Tuftsin Analogue in Inbred Mice with Different Types of Emotional-Stress Reaction, Institute of Pharmacology, Russian Academy of Medical Sciences, Moscow, Zhurnal VND, vol. 48, No. 1, pp. 153-160, 1998 (English-language translation of the full article provided).
Cantor, J.M., et al., "Chronic fluoxetine inhibits sexual behavior in the male rat: reversal with oxytocin," Psychopharmacology (Berl.), vol. 144, pp. 355-362, 1999.
Arletti, R., et al., "Sexual impotence is associated with a reduced production of oxytocin and with an increased production of opioid peptides in the paraventricular nucleus of male rats," Neurosci. Lett., vol. 233, pp. 65-68, 1997.
Semenova, T.P., et al., "Use of Selank to Correct Measures of Integrative Brain Activity and Biogenic Amine Levels in Adult Rats Resulting from Antenatal Hypoxia," Neurosci. Behav. Physiol., vol. 38, No. 2, pp. 203-207, 2008 (Translated from Rossiiskii Fiziologicheskii Zhurnal imeni I. M. Sechenova, vol. 92, No. 11, pp. 1332-1338, 2006).

(Continued)

Primary Examiner — Karlheinz R Skowronek
Assistant Examiner — Lianko Garyu
(74) Attorney, Agent, or Firm — Troutman Sanders LLP

(57) ABSTRACT

The invention relates to a novel agent having an influence on the genital, sexual and reproductive function of mammals and human beings. More specifically, the invention relates to the use of a heptapeptide of the general formula (I) Thr-Lys-Pro-Arg-Pro-Gly-Pro (SEQ ID NO: 1) as a stimulator of the genital, sexual and reproductive function of mammals and human beings. The invention widens the range of agents available for stimulating the genital, sexual and reproductive function of mammals and human beings.

9 Claims, No Drawings

(56) References Cited

OTHER PUBLICATIONS

International Preliminary Examination Report for International Appl. No. PCT/RU2010/000285 mailed on Sep. 23, 2010.
International Preliminary Report on Patentability for International Appl. No. PCT/RU2010/000285 issued on Dec. 6, 2011.
International Search Report dated Sep. 23, 2010 received during the prosecution of International Application No. PCT/RU2010/000285.
Kozlovskaya et al. "A comparative study of the effect of tuftsin fragments on passive avoidance learning characteristics", Pharmaceutical Chemistry Journal, vol. 35, No. 3 (2001) pp. 121-123.
Kozlovskaya et al, "Selank and short peptides of the tuftsin family in the regulation of adaptive behavior in stress", Neuroscience and Behavioral Physiology, vol. 33, No. 9 (2003) pp. 853-860.
Kolomin et al; "Expression of inflammation-related genes in mouse spleen under tuftsin analog Selank"; Regulatory Peptides 170 (2011) 18-23.
Czabak-Garbacz et al.; "Influence of long-term treatment with tuftsin analogue TP-7 on the anxiety-phobic states and body weight", Pharmacological Reports (2006), 58, pp. 562-567.

* cited by examiner

STIMULATOR OF GENITAL, SEXUAL AND REPRODUCTIVE FUNCTION

CROSS REFERENCE TO PRIOR APPLICATIONS

This is a U.S. National Phase application under 35 U.S.C. §371 of International Patent Application No. PCT/RU2010/000285, filed Jun. 1, 2010, which claims the priority of Russian Federation Patent Application No. RU 2009121281, filed Jun. 4, 2009, both of which are incorporated by reference herein. The International Application published in Russian on Dec. 9, 2010 as WO 2010/140926A1 under PCT Article 21(2).

TECHNICAL FIELD OF THE INVENTION

The invention is related to medicine, namely to a new use for a pharma-ceutical agent as a stimulator of genital, sexual, and reproductive function and may be used for the treatment of:
  sexual dysfunction not caused by organic disorders or diseases;
  the absence or loss of sexual attraction;
  aversion to sexual intercourse and absence of sexual pleasure;
  orgasmic dysfunction;
  other sexual dysfunction not caused by organic disorders or disease;

The current significance of this development is determined by the large number of people suffering from sexual dysfunctions (based on the totals from studies by the ACSF group, 43% of women and 31% of men suffer from sexual dysfunction), as well as by an increase in stressful situations in modern life associated with technogenic and natural catastrophes, which are made worse by ecological conditions, urbanization, and destabilization of the political and economic situation in modern society, and by the general trend in the aging of society, which are the principal reasons for the development of sexual and reproductive dysfunctions, as well as by the inadequacy of modern medicine and the lack of adequate methods for treating sexual dysfunctions.

At the present time, with infertility in people and the increase in fecundity in animals, comprehensive long-term treatment is being conducted, including hormonal treatment, antibiotic therapy, desensitizing agents, protein therapy, etc. (A. L. Paducheva, *Gormonal'nyye preparaty v zhivotnovodstve* [Hormonal drugs in animal husbandry]. Moscow: Rossel'khozizdat, 1979: 119-155).

The use of pilastin is known for increasing reproductive capacity in warm-blooded animals (Russian Federation (RF) patent No. 2058791 from 1996).

The use of peptides is known for the treatment of erectile dysfunction (PCT WO 94/22460, U.S. Pat. Nos. 5,955,421 and 5,932,548, and RF patent No. 2264823).

It is known that oxytocin, a nonapeptide containing a disulfide bond, has the structure
  Cys-Tyr-Ile-Gln-Asn-Cys-Pro-Leu-Gly-NH$_2$ (SEQ ID NO: 2),
and is one of the most important regulators of the reproductive sphere in mammals. Oxytocin and its structural analogues obtainable by the methods of chemical synthesis are widely used in medicine and veterinary medicine as medicinal agents (Cantor, J. M., Y. M. Binik, and J. G. Pfaus. Chronic fluoxetine inhibition of sexual behavior in male rats: reversal with oxytocin. Psychopharmacology (Ben), June 1999, vol. 144 (4): 355-362; Arletti, R., L. Calza, and L. Giardiano. Sexual impotence is associated with a reduced production of oxytocin and with increased opioid peptides of the iparaventricular nucleus of male rats. Neurosci. Lett., Sep. 19, 1997, vol. 233(2-3): 65-68).

A heptapeptide of the formula Thr-Lys-Pro-Arg-Pro-Gly-Pro (SEQ ID NO: 1) possesses antianxiety action (Seredinin, S. B., Kozlovskaya, M. M., Blednev, Yu. A., et al. lzucheniye protivotrevozhnogo deistviya analoga endogennogo peptida taftsina na inbrednykh myshah s razlichnym fenotipom emotsyonal'no-stressornoi reaktsii. [Study of the antianxiety action of an analogue of an endogenous peptide, tuftsin, on inbred mice with different phenotypes of emotional-stressor reaction]. VND Zhurnal [VND Journal], 1998, vol. 48, No. 1).

A heptapeptide is known with the formula (I) Thr-Lys-Pro-Arg-Pro-Gly-Pro (SEQ ID NO: 1), as an anxiolytic agent (RF patent No. 2155065 from 1999). However, the possibility of its use as a stimulator of reproductive capacity in mammals has not been described.

DESCRIPTION OF THE INVENTION

A new direction in the area of creating effective and safe medicinal agents for a suitable treatment of:
  sexual dysfunction not caused by organic disorders or diseases;
  the absence or loss of sexual attraction;
  aversion to sexual intercourse and absence of sexual pleasure;
  orgasmic dysfunction;
  other sexual dysfunction not caused by organic disorders or disease;
is the creation of stimulator of genital, sexual, and reproductive function on the basis of endogenous regulatory peptides, highly effective and safe by virtue of their belonging to biological structures related to the organism.

The object of the present invention is the use of a heptapeptide of the formula Thr-Lys-Pro-Arg-Pro-Gly-Pro (SEQ ID NO: 1) according to a novel function as a stimulator of genital, sexual, and reproductive function in mammals.

The technical result of the invention is achieved by the fact that the heptapeptide of the general formula Thr-Lys-Pro-Arg-Pro-Gly-Pro (SEQ ID NO: 1) is used as a stimulator of genital, sexual, and reproductive function.

It is established that the heptapeptide Thr-Lys-Pro-Arg-Pro-Gly-Pro (SEQ ID NO: 1) possesses a broader spectrum of action. The heptapeptide exhibits an optimizing and activating action on the intellectual and cognitive functions of the brain, and it also stimulates genital, sexual, and reproductive functions, which constitutes an important positive part of its specific pharmacological activity.

The possibility of the objective manifestation of the technical result in the use of the invention is confirmed by the reliable data presented in the examples, which contain information of an experimental nature obtained according to procedures adopted in this field.

The problem of studying sexual functions is a serious issue, for a multitude of situational factors, the somatic and mental state of patients, their temperament, and a large number of other factors affect the results. On the other hand, outside of laboratory conditions, it is not possible to establish a number of factors (for example, dilation of the vagina). A number of factors may affect only men (the formation of an orgasmic cuff), and other factors only women. Based on this, the selection of indicators for the characteristics of sexual function is individual, depending on the goals of the investigation. In the present work, a quantified scale of the sexual formula for women (SFW) was adopted as a basis, which is described in detail by G. S. Vasil'chenko in the reference Sexopathologiya [Sex pathology], 1990.

Evaluation of the sexual function in the present investigation was done by both a physician-sexologist (case manager) and by the patient with subsequent refinement of the data by the case manager. Patients reported a change in their condition in a journal every 4 hours after beginning to take the drug, for 24 hours and based on the degree of change in condition over the treatment period. An examination by the sexologist was conducted before treatment and 1, 5, 10, and 15 days after the start of the investigation. At the time of statistical analysis, the physician-sexologist gathered information based on the retention and stability of the effect obtained during the treatment period in people who had completed the course of treatment.

An assessment of sexual function was done based on a point system in accordance with the SFW quantified scale. The quantified scale represents a sexology questionnaire including questions on the state of the mental, secretor, orgasmic, and residual stages of the female copulation cycle (libido, mood, onset of orgasm, physical condition, and mood after performance of the sex act), with points indicated for each response variant.

Sexology studies have their own specifics, presenting special requirements for confidentiality of the information obtained. The failure to meet this requirement can even pervert the results of the investigation. In order to observe the confidentiality of the information and provide patient confidence (excluding a negative psychological factor), a special procedure was developed for reporting data.

At the patient's first visit, the physician gave him/her an individual number (code) and reported the "patient's passport data" (family name, first name, patronymic, contact telephone number) on a Patient List. Based on filling out the Physician's Chart, which contains only the individual code from the indicators identified, the case manager taught the patient the rules for filling out the Patient Chart.

The Patient Chart contained only the individual patient number and the answer codes (A, B. C, . . . , etc.) and it was suggested to report the answers in the codes (scores of 1, 2 . . ., etc.) in accordance with a modified, quantified SFW scale, which was also issued to the patient at the first visit. The patient thereupon kept the sexology questionnaire and the Patient Chart in different places, so that if by chance the cards should fall into the hands of a third party, interpretation of the confidential data would be eliminated.

At a repeat patient visit, the case manager replaced the Patient Chart for the next observation period, attaching the one filled out with the Physician's Chart, analyzed the self-monitoring data, and placed the updated information in the Physician's Chart.

59 patients were studied by this procedure. Among them were women aged 24 to 66 years. The patients studied made up the groups being analyzed:

Group I consisted of 8 healthy women;

Group II consisted of 10 women with sexual dysfunction not caused by other illnesses;

Group III consisted of 31 women with orgasmic dysfunction;

Group IV consisted of women with a pronounced decrease (6 persons) and absence of libido (2 persons);

Group V consisted of 2 women with diagnosed infertility.

The characteristics of the contingent of the study groups are presented in the corresponding sections of the study results. A comparative table of patient condition according to basic sexological function is presented in Table 1.

Statistical processing of the study materials was done on an IBM computer in semiautomated mode using a standard MS Excel 2000 program package. In order to perform the statistical computations, standard statistical formulas were used (Venchikov, A. I. and V. A. Venchikov, 1974; Sergiyenko, V. I. and I. B. Bondareva, 2001), with a subsequent check of the results of examples presented in the literature, with the responses and with the results of calculations based on the Biostat program (Stanton A. Glantz, version 4.03, 1998).

THE BEST EMBODIMENT OF THE INVENTION

Data on analyzed groups of patients are presented in Examples 1-5.

Example 1

The women without obvious impairment of sexual function in Group I (8 persons) took the drug for the purpose of obtaining new sensations. However, sexual-function activity was evaluated by the case manager as moderate; somatic pathology did not come to light. The results of the analysis of using heptapeptide of the general formula Thr-Lys-Pro-Arg-Pro-Gly-Pro (SEQ ID NO: 1) are evidence of its reliable effect on the reinforcement of the sexual function of healthy women (Table 2).

Change in the expression of the manifestation of the principal indicators of sexual function (in points) and the times of onset of the effect (in days) for patients in Group I (n=8) are presented in Table 2.

Onset of the effect in Group I was observed at different times (from Day 1 to Day 15). The drug very rapidly exhibited an effect in reinforcing libido (in the first twenty-four hours) and on the orgasmic stage of the copulation cycle (by Day 10 of the treatment). The dynamics of the appearance of the effect of reinforcing sexual function in patients of Group I (n=8) when administering the heptapeptide of general formula Thr-Lys-Pro-Arg-Pro-Gly-Pro (SEQ ID NO: 1) are presented in Table 3.

At the end of the course of using the heptapeptide of the general formula Thr-Lys-Pro-Arg-Pro-Gly-Pro (SEQ ID NO: 1), the presence of an effect was noted in all the patients in Group I. In half the patients, the effect had already begun by the end of the first twenty-four hours. A guaranteed appearance of results in healthy women may be expected by Day 15.

The dynamics of the state of expression of the indicators of sexual function in the healthy women of Group I (n=8) are presented in Table 4. According to all the indicators, the effect was reliably reinforced, at a score of 1 on the quantified SFW scale.

With the positive dynamics in all the patients of Group I, it is noted that the reinforcement of sexual libido only occurs with its decrease (to a score of 4). Phenomena of hypersexuality, which might be characterized as the appearance of sexual libido several times a day (a score of 6), was not evoked by heptapeptide of the general formula Thr-Lys-Pro-Arg-Pro-Gly-Pro (SEQ ID NO: 1). This may explain the absence of the dynamics of the reinforcement of attraction in the other half of patients, with the daily presence of sexual libido (a score of 5).

On the whole, pronounced, reliable dynamics are detected, based on all the indicators of sexual function. Sex acts occurred daily (in 75% of the women). With rare sex acts (up to several times a month, a score of 3) after a course of taking heptapeptide of the general formula Thr-Lys-Pro-Arg-Pro- Gly-Pro (SEQ ID NO: 1), frequency was increased to daily (a score of 4), and for weekly acts, it increased to daily (a score of 5).

Before taking the drug, healthy women noticed the onset of orgasm in only half of all sex acts (a score of 4); after a course of administration, orgasm began to set in more frequently: in 80-100% of the cases (a score of 5). The reliable dynamics of the general physical state after sex acts are evidence that the pronounced orgasmic release brings, at a minimum, a residual arousal, which is caused by a sensation of the complete conclusion of the sex act, satisfaction, and a pleasant fatigue.

Mood dynamics after the sex act are reliable evidence that the sex act ceased to bear a forced, compulsory character, and began to bring pleasure and the joy of a mutually sharable closeness.

Thus, the analysis results from the use of heptapeptide of the general formula Thr-Lys-Pro-Arg-Pro-Gly-Pro (SEQ ID NO: 1) in healthy women reliably confirm its positive effect on reinforcing sexuality. An insignificant decline in sexuality in healthy women is associated with social conditions: way of life, work conditions, stress, etc. With sexual adaptation to a sex partner with a natural insignificant reduction in sexuality, the drug is capable of reinforcing the expression of the mental and orgasmic phases of the copulation cycle and of reviving a feeling of love and a desire for the sex act.

Attraction to the opposite sex occurred daily, vaginal mucus begins to be secreted more rapidly, orgasm sets in with almost every sexual contact, even repeated orgasmic releases are manifested, after which a feeling of satisfaction and pleasant fatigue follow. The dependence of enjoyment on the menstrual cycle disappeared. The sex act ceased to be an obligation to fulfill a spousal duty, gratitude to the man is manifested for the pleasure experienced, and the level of sexual activity was increased.

Example 2

Sexual dysfunction not caused by organic disorders or diseases (Group II, 10 patients). The state of sexual function in the patients of Group II was evaluated by the case manager as moderately impaired. Change in the expression of the manifestation of the principal indicators of sexual function (in points) and the times of onset of the effect (in days) for patients in Group II (n=10) are presented in Table 5.

The analysis results are evidence of the reliable effect of the drug on the restoration of impaired sexual function of patients in this group.

The times of onset of the effect are somewhat longer than in the patients of Group I. In general, the effect sets in on Days 7-11 of taking the drug. The dynamics of the state of expression of the principal indicators of sexual function for patients in Group II (n=10) are presented in Table 6.

The expression of a pathology was manifested in the reduction of sexual libido to once a week or less often (in 10% of the patients even to once a year), lubrication depended on an internal incentive, which depended strongly on the stage of the menstrual cycle (60%). Orgasm set in, in the majority of patients (60%), in half the cases of sexual contact and less often, (30%). It was caused by the presence of residual arousal, and as a result sex life had become rarer (in the majority, 60%, to once or twice a month) with the same sex partner.

After undergoing the course of treatment with heptapeptide of the formula Thr-Lys-Pro-Arg-Pro-Gly-Pro (SEQ ID NO: 1), libido occurred daily in 70% of the patients, the sex act began to provide intense enjoyment (30%), the aversion to sex reliably disappeared in all the patients, and lubrication and orgasm were increased. Individual cases of orgasm became more regular, to be manifested in half the cases of sexual contact in 60.0% of the patients, while in 40% they began to be manifested at almost every sex act. Its conclusion was caused by a feeling of satisfaction and a pleasant fatigue in 40% of the patients, it did not remain in patients with unfulfilled sexual arousal. Thanks to the positive dynamics of all the indicators of sexual function, 90% of the patients participated in sex acts as often as weekly and daily.

With the analysis results, it is also noted that in general, a reinforcement of sexual function occurs at a score of 1 on the quantified SFW scale, although in 10% of the patients libido was increased with a score of 2.

The dynamics of the onset of the effect of sexual functions (n=10) are presented in Table 7.

The analysis results represented in Table 7 are evidence of the less effective application of the drug in sexual dysfunction not caused by organic disorders or diseases than in healthy women. Thus the effect set in, in no more than 90% of the cases. The effect did not set in prior to Day 1 in a single patient. Effectiveness during a long-term course did not increase after Day 10 of the treatment.

Thus, the use of the heptapeptide in women with sexual dysfunction not caused by organic disorders or diseases exhibited a reliable positive effect on the reinforcement of sexual function. The mental component of the copulation cycle is reinforced in 70.0-90.0%, the secretor component in 60.0%, the orgasmic component in 70.0%, and sexual activity increases in 40% of the women. Restoration of sexual function occurs more slowly compared with the group of healthy women (Group I).

Example 3

Orgasmic dysfunction was observed in 31 patients. The analysis results are evidence of the reliable effect of the heptapeptide on restoration of impaired sexual function in the patients of this group. Change in the expression of manifestation in the principal indicators of sexual function (in points) and the times of onset of the effect (in days) for patients in Group III (n=31) are presented in Table 8.

Based on the case manager's conclusion and the analysis results, the patients of Group III had pronounced impairment of sexual function. The expression of the impairment is presented in Table 9. After undergoing a course of treatment with heptapeptide of the formula Thr-Lys-Pro-Arg-Pro-Gly-Pro (SEQ ID NO: 1), a reliable improvement was revealed in all the indicators of sexual function. It is established that the improvement occurs at a later time than in healthy women. The dynamics of expression of the principal indicators of sexual function in patients of Group III are presented in Table 6.

For the patients in this group, the rare appearance of libido was characteristic (less often than once a month in 74.2% of the patients), indifference (64.5%), and even aversion (6.5%) to sex, whereby the women tried to avoid the sex act. 6.5% of the women had never experienced orgasm (age 25-26 years). After the sex act, 71.0% of the women notice a residual unfulfilled arousal.

After undergoing a course of treatment, libido began to be exhibited weekly (73.9%), the number of patients with an indifferent attitude toward sex was reliably decreased (from 64.5 to 12.9%), protracted preliminary stimulation of the erogenous zones was no longer required to attain lubrication. In 19.4% it began to set in very rapidly, even with the most superficial caresses. In the remainder, its expression depended on the expression of sexual arousal. The onset of orgasm became reliably more frequent (in 63.6% of the patients, in half of all sexual contacts or more often). Unfulfilled sexual arousal after the sex act remained in only 27.3% of the patients. However, sexual activity, in general, remained at the previous level; it increased in only 27.6% of the patients.

With the analysis results, it is also noted that a highly pronounced change in the indicators of sexual function (evaluated at 2 on the SFW scale) during treatment with heptapeptide of the formula Thr-Lys-Pro-Arg-Pro-Gly-Pro (SEQ ID NO: 1) does not yield restoration. Thus, the dynamics were absent for a highly pronounced manifestation of libido (not more often than once a year), aversion to sex, slight lubrication depending on the phase of the menstrual cycle, and the absence of orgasm during sexual contact with its appearance during erotic dreams.

The analysis results are evidence of an increased level of sexual activity with a score of not more than 1 on the quantified SFW scale.

The dynamics of the onset of the effect of improvement in sexual function (n=10) are presented in Table 10.

The effect in orgasmic dysfunction sets in more rarely than in healthy women (Group I). The onset of the effect, based on the majority of indicators of sexual function in patients of Group III, occurred over the extent of the entire 15-day course of treatment. Sexual activity increased in the first week of treatment. Further administration of the drug did not lead to a more pronounced increase in sexual activity. Patients with a slight degree of impairment of sexual function noted the onset of the effect in the second twenty-four hours of treatment (the indicators had expression at a score of 4 on the SFW scale), producing only complaints of the reduction in orgasmic sensations to 1-2 a month.

Thus, the more serious pathology, orgasmic dysfunction, has a somewhat worse prognosis in the treatment of impairment of the sexual sphere. The treatment periods are longer; restoration of sexual function occurs to a less pronounced manifestation of sexual activity. It is possible to expect improvement in the results with subsequent courses of treatment.

Example 4

A pronounced decrease in libido was observed in 8 persons. At the same time, the patients had pronounced impairment and other indicators of sexual function. Analysis results of using heptapeptide of the general formula Thr-Lys-Pro-Arg-Pro-Gly-Pro (SEQ ID NO: 1) in this group of patients. Change in the expression of the manifestation of the principal indicators of sexual function (in points) and times of onset of the effect (in days) for patients in Group IV (n=8) are presented in Table 11.

As a result of the use of the heptapeptide, the attitude of the patients toward sex was reliably changed. The dynamics of expression of the principal indicators of sexual function in patients of Group IV are presented in Table 12.

Libido was completely absent in two of the patients in Group IV (25.0%). The age of these patients was 25-26 years. Both women noted the disappearance of libido and orgasm after birthing. There was no pathology in the pre-birth period, during births, or in the post-birth period. Lactorrhea at the time of taking the heptapeptide was not noted. Birthings for the women were 1-2 years ago. The case manager noted their highly pronounced impairment of sexual function (complete absence of attraction, rare appearance of lubrication, complete disappearance of orgasm, complete physical indifference at the end of the sex act, aversion to sex). These patients denied an effect from taking the heptapeptide, although erotic dreams appeared during which they began to experience orgasm toward the end of the course. For these patients, it was recommended to evaluate the state of the hormonal background (estrogen, progesterone) and to go through a repeat 15-day course of treatment together with the husband. At the time the results of the present study were analyzed, these patients had not begun a repeat course of treatment.

All the patients in Group IV noted indifference to sex. Lubrication began only after protracted erotic stimulation of the surface and deep erogenous zones. In 25% of the patients, orgasm was completely absent; the others also noted rare individual cases of orgasm. The women completed the sex act with unfulfilled sexual arousal. The nature of the pathology depressed the sexual activity, in which connection sex life was not more often as once a week.

The dynamics of the onset of the effect of the principal indicators of sexual function in patients of Group IV (n=8) are presented in Table 13.

The manifestation of the effect in Group IV was noted in only 50% of the cases. These patients had an unpronounced impairment of sexual function. The effect set in at different times with no more than a score of 1 on the quantified SFW scale. The fastest effect noted is an increase in lubrication and onset of orgasm (toward Day 5). The remaining indicators of sexual function were reinforced only toward Day 10. It must also be noted that an increase in orgasm is noted in 75% of the patients. The absence of pronounced changes in the state of sexual function did not increase the level of sexual activity.

Thus, the moderate action of the drug was observed in pronounced impairment of sexual function with a low level of sexual activity and weak libido. Apparently, this is associated with the presence of a concomitant organic pathology of the sexual sphere (hormonal or somatic). The therapy for such patients requires a comprehensive treatment, with the use of modern psychotherapeutic procedures, antioxidants, curing of somatic pathology, and, if necessary, the prescription of hormonal drugs.

Example 5

Action of the heptapeptide in women with infertility. Group V patients. In order to study the action of the heptapeptide on reproductive function, two patients were selected (n=2) with diagnosed secondary infertility.

I. Clinical case.

Brief extract from the disease history:

Patient A, 46 years old, came with complaints of disruption of menstruation of the menometrorrhagia type, persistent pains below the abdomen, and absence of pregnancy for a period of three years.

From the anamnesis:

1. Heredity not burdened, no blood transfusions, allergy anamnesis not burdened.

2. Illnesses suffered:

Childhood infections, chronic gastritis in the remission stage.

3. Menstruation: since the age of 16, for 7 days, every 30 days, abundant, irregular during the last year, without disease. Last menstruation 6 Jan. 2009.

4. Sex life: since the age of 17.

5. Contraception: barrier methods.

Pregnancies: 1 (medical abortion in 1987, without complications).

Gynecological anamnesis:

In 1990, erosion of cervix, diathermalelectrocoagulation (DEC).

General status:

General condition: satisfactory, skin and mucous membranes pale pink, respiration vesicular in lungs, no wheezing, BP 80-120, abdomen soft, not distended, without disease in all sections, stool and diuresis within norms Gynecological status: external sex organs normally developed, with speculum: cervix conical in shape, not eroded, secretions light-colored.

Body of uterus: enlarged to 5-6 weeks. Pregnancy of rounded shape with uneven contours. Appendages not clearly defined, without disease.

Arches and parametrium free.

Diagnosis: pre-menopausal. Mioma of the uterus in conjunction with adenomiosis. Infertility 2 (second), endometriosis.

Treatment provided:
1. Surgical treatment.
2. Agonists: gonadotropin-releasing hormones (GT-RH): Zonadex 3.6 mg subcutaneously once a month for 6 months.

After treatment provided for a year, pregnancy did not ensue. The patient was given a course of treatment with a 0.1% solution of heptapeptide of the formula Thr-Lys-Pro-Arg-Pro-Gly-Pro (SEQ ID NO: 1) for 15 days intranasally. After administering the treatment, for 3 months, pregnancy ensued. Pregnancy was diagnosed on the basis of data obtained from:
1. Express test for pregnancy,
2. Ultrasound diagnostics,
3. By the laboratory method (β-pure gas radiochromatography-chorion gonadotropy).

II. Clinical case. Brief extract from the disease history:

Patient B, 42 years old, came with complaints of disruption of menstruation of the oligomenorrheal type, absence of pregnancy for 2.5 years. From the anamnesis:

1. Heredity not burdened, no blood transfusions, allergy anamnesis not burdened.
2. Illnesses suffered: childhood infections, hypertony, stage 1; gallstones, in remission stage.
3. Menstruation: since age of 14, for 4-5 days, every 20 days, moderate, irregular during last two years, without disease. Last menstruation 20 Jan. 2009.
4. Sex life: since the age of 20.
5. Contraception: hormonal.
6. Pregnancies: 2 (births: one in 1995, without peculiarities, medical abortion in 1998, without complications).

Gynecological anamnesis: chronic adnexitis in remission stage.

In 1996, erosion of cervix, diathermalelectrocoagulation (DEC).

General status:

General condition: satisfactory, skin and mucous membranes pale pink, respiration vesicular in lungs, no wheezing, BP 95-130, abdomen soft, not distended, without disease in all sections, stool and diuresis within norms.

Gynecological status: external sex organs normally developed, with speculum: cervix cylindrical in shape, not eroded, secretions light-colored.

Body of uterus of normal size, not enlarged, without disease upon palpation, appendages not clearly defined, without disease, arches and parametrium free.

Diagnosis: Late reproductive period, infertility 2 (second), endocrine form.

Treatment provided: 0.1% solution of heptapeptide of the formula Thr-Lys-Pro-Arg-Pro-Gly-Pro (SEQ ID NO: 1) intranasally for 30 days. After administering treatment for 4 months, pregnancy ensued, pregnancy diagnosed on the basis of data obtained from:

1. Express test for pregnancy,
2. Ultrasound diagnostics,
3. By the laboratory method (β-pure gas radiochromatography-chorion gonadotropy).

These two clinical cases allow it to be established that the effect of heptapeptide of the formula Thr-Lys-Pro-Arg-Pro-Gly-Pro (SEQ ID NO: 1) on reproductive function is positive and stimulating. It is worthwhile to mention that in all cases, pregnancy ensued without a change of partner and without providing additional treatment.

Example 6

For 2 months, experiments were conducted on 45 rats of the Hunter strain to study the effect of heptapeptide of the formula Thr-Lys-Pro-Arg-Pro-Gly-Pro (SEQ ID NO: 1) on reproductive behavior in rats. The experiments were conducted in several series: series 1: 15 rats (3 groups, consisting of 4 males and 1 female); series 2: 8 rats (4 pairs of 1 male and 1 female); series 3: 8 rats (4 pairs of 1 male and 1 female with organic CNS lesions); series 4: 8 rats of declining years (more than 2 years); series 5: control animals (8 individuals).

The effect of heptapeptide of the formula Thr-Lys-Pro-Arg-Pro-Gly-Pro (SEQ ID NO: 1) on the reproductive behavior of rats was studied using different methods for its introduction (intramuscularly, intra-peritoneally, and intranasally) in different dosages (25-100 μg/animal).

It is found that intranasal administration of the heptapeptide of the formula Thr-Lys-Pro-Arg-Pro-Gly-Pro (SEQ ID NO: 1) for 10-15 min caused, in all the study groups of animals, pronounced behavioral changes, including an increase in interest and "friendly" behavior with regard to other individuals; elements of "courting" appearing with attempts at coupling. The rats performed grooming of themselves (autogrooming) and other individuals (allogrooming). A distinctly pronounced ano-genital examination of another individual was observed in the rats. The latter consists of a cluster of behavioral reactions, including crawling beneath an individual of the opposite sex, sniffing its ano-genital area, and grooming it. Elements characteristic of coupling were observed not only in the evening but in the daytime as well. In old animals and ones operated on (destruction of the hippocampus, occlusion of the carotid artery) against a background of heptapeptide of the formula Thr-Lys-Pro-Arg-Pro-Gly-Pro (SEQ ID NO: 1), the freezing reaction disappeared, which is a behavioral stress marker.

It is established that the heptapeptide of the formula Thr-Lys-Pro-Arg-Pro-Gly-Pro (SEQ ID NO: 1) brought about a pronounced reinforcing effect on the reproductive function of rats. Against the drug background, the birth rate of the rats increased by 3-5 times. The number of offspring increased up to 12-15 young (for a norm in intact Khanter rats of 5-6). A characteristic feature was that fact that new-born baby rats were of greater weight: 4-5 g (2-3 g for intact ones). A study of the dynamics of the development of offspring in the period of post-natal ontogenesis showed that this pattern of investigative activity (heavier young), their high survival rate, earlier (even in the blind baby rats) strengthening of motor activity, takes place against the background of heptapeptide of the formula Thr-Lys-Pro-Arg-Pro-Gly-Pro (SEQ ID NO: 1) takes place in all the study groups of experimental animals.

Against the background of heptapeptide of the formula Thr-Lys-Pro-Arg-Pro-Gly-Pro (SEQ ID NO: 1) in groups of 1-1.5 month-old baby rats (10 individuals: group 1, 12 individuals: group 2), reinforcement was evident in agonistic relations, a "friendly" attitude with regard to individuals of one sex (males), reinforcement of play activity, absence of aggressive reactions in relation to the experimenter, facilitation of handling reactions (the animals were "tame"). It must be emphasized that, compared with intact young, the faster development of conditioned reflexes was observed in these baby rats (in combination 4-5), and in the intact ones, only in combination 13-15 and toward the 2nd experimental day. Of characteristic features of the effect of the heptapeptide of the formula Thr-Lys-Pro-Arg-Pro-Gly-Pro (SEQ ID NO: 1), reinforcement must be related to the strengthening of maternal instincts and elimination of aggression, which is specific to feeding females with respect to the experimenter. Against the drug background, feeding females took young from other individuals (a phenomenon not peculiar to intact rats, which ate "foreign" young). The reinforcing effect on the reproductive behavior of rats was prolonged (up to 1.5-2 months). Lastly, it is concluded, in the 2nd group of animals (8 rats of 4 pairs: 1 male and 1 female), with the secondary process of coupling occurring early, against a background of feeding the young whose eyes were not yet open. Study of the role of heptapeptide of the formula Thr-Lys-Pro-Arg-Pro-Gly-Pro (SEQ ID NO: 1) in reproductive activity on old rats showed that the reinforcing effect of the drug on reproductive function also takes place in these animals. So in the rats (older than 2 years), in the norm in which maceration of the fetus in the womb of the mother takes place in 70% of the cases or absence of pregnancy in 85%, birth of live offspring was exhibited. However, compared to younger animals, the number of newborns was fewer (up to 5-6 individuals). Considering the presence of compensatory effects of the drug in different cerebral pathologies (brain ischemia, cranio-cerebral traumas), the effect of the heptapeptide of the formula Thr-Lys-Pro-Arg-Pro-Gly-Pro (SEQ ID NO: 1) was studied in a series of special experiments on reproductive function in rats with organic pathologies (unilateral occlusion of the carotid artery and uni- and bilateral destruction of the hippocampus). The data obtained are evidence that the effect of the heptapeptide of the formula Thr-Lys-Pro-Arg-Pro-Gly-Pro (SEQ ID NO: 1) on reproductive function takes place in these rats. However, the series of these experiments is not yet concluded, since at the moment the females are in the pregnancy stage.

Analysis of the data obtained allows the conclusion to be drawn that the heptapeptide of the formula Thr-Lys-Pro-Arg-Pro-Gly-Pro (SEQ ID NO: 1) contributes to eliminating neurotic disturbances and inhibition occurring in laboratory rats, reinforces "courting" processes and grooming peculiar to this species of animal, contributes to coupling not only at night but in the daytime as well, and increases reproductive function. The latter is reflected in the greater number and higher quality of offspring. More pronounced effects on the reproductive function of rats take place with double intranasal administration of the heptapeptide of the formula Thr-Lys-Pro-Arg-Pro-Gly-Pro (SEQ ID NO: 1) in small (25 µg/animal) doses in groups consisting of pairs (1 female+1 male).

INDUSTRIAL APPLICABILITY

Men with impairment of sexual function (10 men) took the drug for the purpose of obtaining new sensations. However, the activity of sexual functioning was evaluated by the case manager as being reduced. Analysis results of using heptapeptide of the general formula Thr-Lys-Pro-Arg-Pro-Gly-Pro (SEQ ID NO: 1) are evidence of its reliable effect on the reinforcement of sexual function of the men (Table 14).

Change in the expression of the manifestation of principal indicators of sexual function (in points) and the times of onset of the effect (in days) for patients in Group I (n=8) are presented in Table 14.

Onset of the effect in Group I was observed at different times (from Day 1 to Day 15). The drug exhibited a very rapid effect on increasing the need for sexual relations (during the first twenty-four hours) and on erection. The dynamics of the appearance of the effect of reinforcing sexual function in patients of Group I (n=8) when administering the heptapeptide of general formula Thr-Lys-Pro-Arg-Pro-Gly-Pro (SEQ ID NO: 1) are presented in Table 15.

At the end of the course of administering the heptapeptide of the formula Thr-Lys-Pro-Arg-Pro-Gly-Pro (SEQ ID NO: 1), the presence of the effect was noted in all the patients in Group I. In half the patients, the effect had already begun by the end of the first twenty-four hours. A guaranteed appearance of results may be expected in men toward Day 15.

According to all the indicators, the effect was reliably reinforced with a score of 1 on the quantified Sexual Function for Men (SFM) scale. The dynamics of the state of expression of the indicators of sexual function in the men of group I (n=10) are presented in Table 16.

On the whole, pronounced, reliable dynamics are found on the basis of all the indicators of sexual function. Sex acts occurred daily. With rare sex acts (up to several times a month), after a course of taking the heptapeptide of the general formula Thr-Lys-Pro-Arg-Pro-Gly-Pro (SEQ ID NO: 1), frequency increased to weekly, while with weekly acts, it increased to daily.

Thus, the results of the analysis of using the heptapeptide of the general formula Thr-Lys-Pro-Arg-Pro-Gly-Pro (SEQ ID NO: 1) in men reliably confirm its positive effect on reinforcing sexuality. An insignificant decline in sexuality in men is associated with social conditions: way of life, work conditions, stress, etc. In sexual adaptation to a sex partner with a natural insignificant decrease in sexuality, the drug is capable of reinforcing the expression of the mental and orgasmic phases of the copulation cycle and reviving a feeling of love and a desire for the sex act.

Attraction toward the opposite sex became daily, orgasm set in at almost every sexual contact, after which followed a feeling of satisfaction and pleasant fatigue. The sex act ceased to be an obligation to fulfill a spousal duty, gratitude to the man was manifested for the pleasure experienced, and the level of sexual activity was increased.

The invention expands the arsenal of agents stimulating reproductive activity in mammals and humans.

The technical result attainable in executing the invention is the discovery of a broad spectrum of medical action for a known stimulator of memory, which defines the possibility of its use in low dosages as a stimulator of genital, sexual, and reproductive function without undesirable side effects, with good tolerability.

TABLE 1

| Indicator of sexual function | Study groups | | | | |
| --- | --- | --- | --- | --- | --- |
| | I (n = 8) | II (n = 10) | III (n = ~31) | IV (n = 8) | V (n = 2) |
| A. Libido | 4.5 | 3.5 | 3.2 | 2.5 | |
| B. Attitude toward sexual activity | 4.0 | 3.5 | 3.2 | 3.0 | |
| C. Lubrication | 4.0 | 3.5 | 3.2 | 2.8 | |
| D. Onset of orgasm | 4.0 | 3.7 | 3.2 | 2.5 | |

TABLE 1-continued

| Indicator of sexual function | I (n = 8) | II (n = 10) | III (n = −31) | IV (n = 8) | V (n = 2) |
|---|---|---|---|---|---|
| E. General physical state after sexual acts | 4.0 | 3.7 | 3.2 | 2.8 | |
| F. Mood after sexual acts | 4.0 | 3.7 | 3.4 | 2.8 | |
| G. Level of sexual activity | 3.8 | 3.4 | 2.9 | 3.0 | |

Study groups

TABLE 2

| Indicator of sexual function | Before treatment | After treatment | Mean time for onset of effect |
|---|---|---|---|
| A. Libido | 4.0 | 5.0 | 1.0 (n = 4) |
| B. Attitude toward sexual activity | 4.0 | 5.0 | 10.8 |
| C. Lubrication | 4.0 | 5.0 | 10.8 |
| D. Onset of orgasm | 4.0 | 5.0 | 5.8 |
| E. General physical state after sexual acts | 4.0 | 4.7 | 10.8 |
| F. Mood after sexual acts | 4.0 | 5.0 | 10.8 |
| G. Level of sexual activity | 3.8 | 4.7 | 10.8 |

TABLE 3

| Indicator of sexual function | Days of drug administration | | | |
|---|---|---|---|---|
| | 1 | 5 | 10 | 15 |
| A. Libido | 8 (100%) | 8 (100%) | 8 (100%) | 8 (100%) |
| B. Attitude toward sexual activity | 4 (50%) | 4 (50%) | 8 (100%) | 8 (100%) |
| C. Lubrication | 4 (50%) | 4 (50%) | 8 (100%) | 8 (100%) |
| D. Onset of orgasm | 4 (50%) | 8 (100%) | 8 (100%) | 8 (100%) |
| E. General physical state after sexual acts | 4 (50%) | 4 (50%) | 8 (100%) | 8 (100%) |
| F. Mood after sexual acts | 4 (50%) | 4 (50%) | 8 (100%) | 8 (100%) |
| G. Level of sexual activity | 4 (50%) | 4 (50%) | 8 (100%) | 8 (100%) |

TABLE 4

| Indicator of sexual function | Before treatment | After treatment |
|---|---|---|
| A. Libido | | |
| 4 (weekly) | 4 (50%) | 0 (0%) |
| 5 (daily) | 4 (50%) | 8 (100%) |
| 6 (several times a day) | 0 (0%) | 0 (0%) |
| B. Attitude toward sexual activity | | |
| 4 (enjoyment depends on menesis) | 8 (100%) | 0 (0%) |
| 5 intense enjoyment) | 0 (0%) | 8 (100%) |
| C. Lubrication | | |
| 4 (depends on presence of attraction) | 8 (100%) | 0 (0%) |
| 5 (sets in rapidly) | 0 (0%) | 8 (100%) |
| D. Onset of orgasm | | |
| 4 (in half of the sex acts) | 8 (100%) | 0 (0%) |
| 5 (more than 80% of the sex acts) | 0 (0%) | 8 (100%) |
| E. General physical state after sex acts | | |
| 4 (sensation of a release of arousal) | 8 (100%) | 0 (0%) |
| 5 (satisfaction and fatigue) | 0 (0%) | 8 (100%) |

TABLE 4-continued

| Indicator of sexual function | Before treatment | After treatment |
|---|---|---|
| F. Mood after sex acts | | |
| 4 (recognition of duty fulfilled) | 8 (100%) | 2 (25%) |
| 5 (feeling of gratitude to man) | 0 (0%) | 6 (75%) |
| G. Level of sexual activity | | |
| 3 (monthly) | 2 (25%) | 0 (0%) |
| 4 (weekly) | 6 (75%) | 2 (25%) |
| 5 (daily) | 0 (0%) | 6 (75%) |

TABLE 5

| Indicator of sexual function | Before treatment | After treatment | Mean time for onset of effect, days |
|---|---|---|---|
| A. Libido | 3.5 | 5.0 | 10.0 |
| B. Attitude toward sexual activity | 3.5 | 5.0 | 11.0 |
| C. Lubrication | 3.5 | 5.0 | 7.0 |
| D. Onset of orgasm (n = 33) | 3.5 | 4.5 | 10.0 |
| E. General physical state after sexual acts (n = 33) | 3.5 | 4.5 | 7.0 |
| F. Mood after sexual acts (n = 33) | 3.0 | 4.5 | 9.0 |
| G. Level of sexual activity (n = 27) | 3.0 | 4.0 | 11.0 |

TABLE 6

| Indicator of sexual function | Before treatment | After treatment |
|---|---|---|
| A. Libido | | |
| 2 (yearly) | 3 (30%) | 0 (0%) |
| 3 (monthly) | 7 (70%) | 1 (10%) |
| 4 (weekly) | 0 (0%) | 2 (20%) |
| 5 (daily) | 0 (0%) | 7 (70%) |
| 6 (several times a day) | 0 (0%) | 0 (0%) |
| B. Attitude toward sexual activity | | |
| 2 (aversion to the sex act) | 1 (10%) | 0 (0%) |
| 3 (indifference toward the sex act) | 8 (80%) | 0 (0%) |
| 4 (enjoyment depends on menesis) | 1 (10%) | 7 (70%) |
| 5 (intense enjoyment) | 0 (0%) | 3 (30%) |
| C. Lubrication | | |
| 2 (rarely emerges) | 1 (10%) | 0 (0%) |
| 3 (with protracted stimulation) | 3 (30%) | 1 (10%) |
| 4 (depends on presence of attraction) | 6 (60%) | 7 (70%) |
| 5 (sets in rapidly) | 0 (0%) | 2 (20%) |
| D. Onset of orgasm | | |
| 3 (single occurrences) | 4 (40%) | 0 (0%) |
| 4 (in half of the sex acts) | 6 (60%) | 3 (30%) |
| 5 (more than 80% of the sex acts) | 0 (0%) | 7 (70%) |
| E. General physical state after sex acts | | |
| 3 (unfulfilled arousal) | 4 (40%) | 0 (0%) |
| 4 (sensation of release of arousal) | 6 (60%) | 60 (60%) |
| 5 (satisfaction and fatigue) | 0 (0%) | 4 (40%0 |
| F. Mood after sex acts | | |
| 3 (complete indifference) | 30 (30%) | 1 (10%) |
| 4 (recognition of duty fulfilled) | 7 (70%) | 3 (30%) |
| 5 (feeling of gratitude toward man) | 0 (0%) | 6 (60%) |
| G. Level of sexual activity | | |
| 3 (monthly) | 7 (70%) | 1 (10%) |
| 4 (weekly) | 3 (30%) | 7 (70%) |
| 5 (daily) | 0 (0%) | 2 (20%) |

TABLE 7

| Indicator of sexual function | Days of drug administration | | | |
|---|---|---|---|---|
| | 1 | 5 | 10 | 15 |
| A. Libido | 0 (0%) | 1 (10%) | 9 (90%) | 9 (90%) |
| B. Attitude toward sexual activity | 0 (0%) | 2 (20%) | 7 (70%) | 7 (70%) |
| C. Lubrication | 0 (0%) | 3 (30%) | 7 (70%) | 7 (70%) |
| D. Onset of orgasm | 0 (0%) | 2 (20%) | 7 (70%) | 7 (70%) |
| E. General physical state after sexual acts | 0 (0%) | 3 (30%) | 8 (80%) | 8 (80%) |
| F. Mood after sexual acts | 0 (0%) | 2 (20%) | 5 (50%) | 5 (50%) |
| G. Level of sexual activity | 0 (0%) | 1 (10%) | 4 (40%) | 4 (40%) |

TABLE 8

| Indicator of sexual function | Before treatment | After treatment | Mean time for onset of effect, days |
|---|---|---|---|
| A. Libido | 3.2 | 4.0 | 5.5 |
| B. Attitude toward sexual activity | 3.2 | 4.0 | 10.7 |
| C. Lubrication | 3.2 | 3.9 | 10.3 |
| D. Onset of orgasm | 3.2 | 3.9 | 10.5 |
| E. General physical state after sexual acts | 3.2 | 4.0 | 10.7 |
| F. Mood after sexual acts | 3.4 | 3.9 | 10.6 |
| G. Level of sexual activity | 2.9 | 3.2 | 5.0 |

TABLE 9

| Indicator of sexual function | Before treatment | After treatment |
|---|---|---|
| A. Libido | | |
| 2 (yearly) | 2 (6.5%) | 2 (6.5%) |
| 3 (monthly) | 21 (67.7%) | 4 (12.9%) |
| 4 (weekly) | 8 (25.8%) | 17 (54.8%) |
| 5 (daily) | 0 (0.0%) | 8 (25.8%) |
| 6 (several times a day) | 0 (0.0%) | 0 (0.0%) |
| B. Attitude toward sexual activity | | |
| 2 (aversion to the sex act) | 2 (6.5%) | 2 (6.5%) |
| 3 (indifference toward the sex act) | 20 (64.5%) | 4 (12.9%) |
| 4 (enjoyment depends on menesis) | 9 (29.0%) | 17 (54.8%) |
| 5 (intense enjoyment) | 0 (0.0%) | 8 (25.8%) |
| C. Lubrication | | |
| 2 (rarely emerges) | 2 (6.5%) | 2 (6.5%) |
| 3 (with protracted stimulation) | 22 (71.0%) | 4 (12.9%) |
| 4 (depends on presence of attraction) | 7 (22.6%) | 19 (61.3%) |
| 5 (sets in rapidly) | 0 (0.0%) | 6 (19.4%) |
| D. Onset of orgasm | | |
| 1 (never experienced orgasm) | 2 (6.5%) | 2 (6.5%) |
| 2 (only during erotic dreams) | 0 (0.0%) | 0 (0.0%) |
| 3 (single occurrences) | 20 (64.5%) | 6 (19.4%) |
| 4 (in half of the sex acts) | 9 (29.0%) | 15 (48.4%) |
| 5 (more than 80% of the sex acts) | 0 (0.0%) | 8 (25.8%) |
| E. General physical state after sex acts | | |
| 2 (complete physical indifference) | 2 (6.5%) | 2 (6.5%) |
| 3 (unfulfilled arousal) | 20 (64.5%) | 4 (12.9%) |
| 4 (sensation of a release of arousal) | 9 (29.0%) | 17 (54.8%) |
| 5 (satisfaction and fatigue) | 0 (0.0%) | 8 (25.8%) |
| F. Mood after sex acts | | |
| 2 (escape from obligation) | 2 (6.5%) | 2 (6.5%) |
| 3 (complete indifference) | 16 (51.6%) | 6 (19.4%) |
| 4 (recognition of duty fulfilled) | 13 (41.9%) | 15 (48.4%) |
| 5 (feeling of gratitude toward man) | 0 (0.0%) | 8 (25.8%) |

TABLE 9-continued

| Indicator of sexual function | Before treatment | After treatment |
|---|---|---|
| G. Level of sexual activity | | |
| 2 (yearly) | 4 (12.9%) | 4 (12.9%) |
| 3 (monthly) | 25 (80.6%) | 17 (54.8%) |
| 4 (weekly) | 2 (6.5%) | 10 (32.3%) |
| 5 (daily) | 0 (0%) | 0 (0%) |

TABLE 10

| Indicator of sexual function | Days of drug administration | | | |
|---|---|---|---|---|
| | 1 | 5 | 10 | 15 |
| A. Libido | 8 (100%) | 12 (38.7%) | 21 (67.7%) | 25 (80.6%) |
| B. Attitude toward sexual activity | 6 (19.4%) | 8 (25.8%) | 16 (51.6%) | 24 (77.4%) |
| C. Lubrication | 6 (19.4%) | 12 (38.7%) | 16 (51.6%) | 24 (77.4%) |
| D. Onset of orgasm | 6 (19.4%) | 12 (38.7%) | 14 (45.2%) | 22 (71.0%) |
| E. General physical state after sexual acts | 6 (19.4%) | 8 (25.8%) | 14 (45.2%) | 24 (77.4%) |
| F. Mood after sexual acts | 6 (19.4%) | 8 (25.8%) | 12 (38.7%) | 20 (64.5%) |
| G. Level of sexual activity | 6 (19.4%) | 8 (25.8%) | 8 (25.8%) | 8 (25.8%) |

TABLE 11

| Indicator of sexual function | Before treatment | After treatment | Time for onset of effect, days |
|---|---|---|---|
| A. Libido | 2.5 | 4.0 | 10.0 |
| B. Attitude toward sexual activity | 3.5 | 4.0 | 10.0 |
| C. Lubrication | 2.8 | 4.0 | 10.0 |
| D. Onset of orgasm | 2.5 | 4.0 | 10.0 |
| E. General physical state after sexual acts (n = 33) | 2.8 | 4.5 | 15.0 |
| F. Mood after sexual acts | 2.8 | 4.5 | 15.0 |
| G. Level of sexual activity | 3.0 | 4.5 | — |

TABLE 12

| Indicator of sexual function | Before treatment | After treatment |
|---|---|---|
| A. Libido | | |
| 1 (entirely absent) | 2 (25%) | 2 (25%) |
| 2 (yearly) | 0 (0%) | 0 (0%) |
| 3 (monthly) | 6 (75%) | 2 (25%) |
| 4 (weekly) | 0 (0%) | 4 (50%) |
| 5 (daily) | 0 (0%) | 0 (0%) |
| 6 (several times a day) | 0 (0%) | 0 (0%) |
| B. Attitude toward sexual activity | | |
| 3 (indifference toward the sex act) | 8 (100%) | 4 (50%) |
| 4 (enjoyment depends on menesis) | 0 (0%) | 4 (50%) |
| 5 (intense enjoyment) | 0 (0%) | 0 (0%) |
| C. Lubrication | | |
| 2 (rarely emerges) | 2 (25%) | 2 (25%) |
| 3 (with protracted stimulation) | 6 (75%) | 2 (25%) |
| 4 (depends on presence of attraction) | 0 (0%) | 4 (50%) |
| 5 (sets in rapidly) | 0 (0%) | 0 (0%) |

TABLE 12-continued

| Indicator of sexual function | Before treatment | After treatment |
|---|---|---|
| D. Onset of orgasm | | |
| 1 (never experienced orgasm) | 2 (25%) | 0 (0%) |
| 2 (only during erotic dreams) | 0 (0%) | 2 (25%) |
| 3 (single occurrences) | 6 (75%) | 2 (25%) |
| 4 (in half of the sex acts) | 0 (0%) | 4 (50%) |
| 5 (more than 80% of the sex acts) | 0 (0%) | 0 (0%) |
| E. General physical state after sex acts | | |
| 2 (complete physical indifference) | 2 (25%) | 2 (25%) |
| 3 (unfulfilled arousal) | 6 (75%) | 2 (25%) |
| 4 (sensation of a release of arousal) | 0 (0%) | 4 (50%) |
| 5 (satisfaction and fatigue) | 0 (0%) | 0 (0%) |
| F. Mood after sex acts | | |
| 2 (escape from obligation) | 2 (25%) | 2 (25%) |
| 3 (complete indifference) | 6 (75%) | 2 (25%) |
| 4 (recognition of duty fulfilled) | 0 (0%) | 4 (50%) |
| 5 (feeling of gratitude toward man) | 0 (0%) | 0 (0%) |
| G. Level of sexual activity | | |
| 3 (monthly) | 8 (100%) | 4 (50%) |
| 4 (weekly) | 0 (0%) | 4 (50%) |
| 5 (daily) | 0 (0%) | 0 (0%) |

TABLE 13

| Indicator of sexual function | Days of drug administration | | | |
|---|---|---|---|---|
| | 1 | 5 | 10 | 15 |
| A. Libido | 0 (0%) | 0 (0%) | 4 (50%) | 4 (50%) |
| B. Attitude toward sexual activity | 0 (0%) | 0 (0%) | 4 (50%) | 4 (50%) |
| C. Lubrication | 0 (0%) | 4 (50%) | 4 (50%) | 4 (50%) |
| D. Onset of orgasm | 0 (0%) | 4 (50%) | 4 (50%) | 6 (75%) |
| E. General physical state after sexual acts | 0 (0%) | 0 (0%) | 4 (50%) | 4 (50%) |
| F. Mood after sexual acts | 0 (0%) | 0 (0%) | 4 (50%) | 4 (50%) |
| G. Level of sexual activity | 0 (0%) | 0 (0%) | 0 (0%) | 0 (%) |

TABLE 14

| Indicator of sexual function | Before treatment | After treatment | Mean time for onset of effect |
|---|---|---|---|
| A. Need for sexual relations | 1.6 | 2.5 | 1.0 |
| B. Mood before sexual intercourse | 1.4 | 2.9 | 10.8 |
| C. Sexual spirit | 1.3 | 2.4 | 10.8 |
| D. Tension of sex organ (erection) | 1.1 | 2.7 | 5.8 |
| E. Duration of sexual intercourse | 0.75 | 2.8 | 10.8 |
| F. Frequency of sexual performances | 1.5 | 2.5 | 10.8 |
| G. Mood after sex acts | 1.5 | 2.8 | 10.8 |

TABLE 15

| Indicator of sexual function | Days of drug administration | | | |
|---|---|---|---|---|
| | 1 | 5 | 10 | 15 |
| A. Need for sexual relations | 8 (100%) | 8 (100%) | 8 (100%) | 8 (100%) |
| B. Mood before sexual intercourse | 4 (50%) | 4 (50%) | 8 (100%) | 8 (100%) |
| C. Sexual spirit | 4 (50%) | 4 (50%) | 8 (100%) | 8 (100%) |
| C. Erection | 4 (50%) | 8 (100%) | 8 (100%) | 8 (100%) |
| E. Duration of sexual intercourse | 4 (50%) | 4 (50%) | 8 (100%) | 8 (100%) |
| F. Frequency of sexual performances | 4 (50%) | 4 (50%) | 8 (100%) | 8 (100%) |
| G. Mood after sex act | 4 (50%) | 4 (50%) | 8 (100%) | 8 (100%) |

TABLE 16

Family name, first name, patronymic
Bachelor. Married. Divorced.

| | | Before treatment | After treatment |
|---|---|---|---|
| I. Need for sexual relations | | | |
| How often does the urgent desire arise to perform a sex act (other than dependence on the tension of the sex organ): | | | |
| generally never or not more often than once a year | 0 | | |
| several times a year, but not more often than once a month | 1 | 4 (40%) | |
| two to four times a month | 2 | 6 (6.0%) | 3 (30%) |
| twice or several times a week | 3 | | 6 (60%) |
| once or several times every twenty-four hours | 4 | | 1 (10%) |
| II. Mood before sexual intercourse | | | |
| strong fear of failure, and therefore attempt was never consummated | 0 | 1 (10%) | |
| pronounced uncertainty, and therefore I look for an excuse to avoid the attempt | 1 | 4 (40%) | |
| some uncertainty, but I don't avoid the attempt (or, I perform the sex act to please the wife, without inner incentive; or, I perform intercourse to test myself) | 2 | 5 (50%) | 1 (10%) |
| mainly, the desire for enjoyment, possession of a woman, and for intercourse without apprehension | | | 9 (90%) |
| always only craving for enjoyment by the woman; I never experience the least doubt | 4 | | |

TABLE 16-continued

Family name, first name, patronymic
Bachelor. Married. Divorced.

| | | Before treatment | After treatment |
|---|---|---|---|
| III. Sexual spirit | | | |
| I perform actions intended for the immediate achievement of a sex act | | | |
| I generally do not perform or I perform at intervals of not less than a year | 0 | | |
| several times a year, but not more often than once a month | 1 | 7 (70%) | |
| several times a month, but not more often than once a week | 2 | 3 (30%) | 6 (60%) |
| twice or several times a week | 3 | | 4 (40%) |
| once or several times every twenty-four hours | 4 | | |
| IV. Tension of sex organ (erection) | | | |
| erection does not occur under any circumstances | 0 | 1 (10%) | |
| aside from the situation of the sex act, erection is sufficient; however at the time of sexual intercourse, it becomes flaccid, introduction of the organ is not successful | 1 | 8 (80%) | |
| It is necessary to apply force or local manipulation to bring about an erection sufficient for introduction (or else the erection becomes flaccid after introduction but before ejaculation of semen) | 2 | 1 (10%) | 3 (30%) |
| erection incomplete, but introduction is successful without a problem | 3 | | 7 (70%) |
| erection occurs under any conditions, even very unfavorable ones | 4 | | |
| V. Duration of sexual intercourse | | | |
| Ejaculation occurs: | | | |
| does not occur under any circumstances | 0 | | |
| does not occur at every sex act, intercourse bears a prolonged, sometimes exhausting character | 0.5 | 7 (70%) | |
| even before introduction of the sex organ or at the time of introduction | 1 | 2 (20%) | |
| several seconds after introduction | 2 | 1 (10%) | |
| approximately within 15-20 movements | 2.5 | | 4 (40%) |
| within 1-2 minutes | 3 | | 6 (60%) |
| more than 2 minutes (indicate approximate duration) | 4 | | |
| VI. Frequency of sexual performances | | | |
| Ejaculation occurs during intercourse (or night ejaculations, onanism, and other things) on the average: | | | |
| generally does not occur or occurs no more often than once a year | 0 | | |
| several times a year, but not more often than once a month | 1 | 5 (50%) | |
| several times a month, but not more often than once a week | 2 | 5 (50%) | 5 (50%) |
| twice or several times a week | 3 | | 4 (40%) |
| once or several times every twenty-four hours | 4 | | 1 (10%) |
| VI. Mood after sexual intercourse (or an unsuccessful attempt) | | | |
| extreme depression, sensation of catastrophe (or aversion to wife) | 0 | | |
| disappointment, vexation | 1 | 6 (60%) | |
| indifference (somewhat upset due to knowledge that the woman feels unsatisfied) | 2 | 3 (30%) | 4 (40%) |
| satisfaction and pleasant fatigue | 3 | 1 (10%) | 4 (40%) |
| complete satisfaction and spiritual uplift | 4 | | 2 (20%) |

The invention claimed is:

1. A method for stimulating genital, sexual, or reproductive function in a mammal in need thereof comprising administering to said mammal a heptapeptide having general formula (I): Thr-Lys-Pro-Arg-Pro-Gly-Pro (SEQ ID NO: 1).

2. The method of claim 1, wherein the mammal is human.

3. The method of claim 1, wherein the mammal has a condition selected from the group consisting of sexual dysfunctions not caused by organic disorders or diseases, the absence or loss of sexual attraction, aversion to sexual intercourse, absence of sexual pleasure, and orgasmic dysfunction.

4. The method of claim 1, comprising administering the heptapeptide intranasally for at least 10 days.

5. The method of claim 1, comprising administering the heptapeptide intranasally for at least 15 days.

6. A method for treating a condition in a mammal in need of such treatment comprising administering to said mammal a heptapeptide having general formula (I): Thr-Lys-Pro-Arg-Pro-Gly-Pro (SEQ ID NO: 1), wherein the condition is selected from the group consisting of sexual dysfunctions not caused by organic disorders or diseases, the absence or loss of sexual attraction, aversion to sexual intercourse, absence of sexual pleasure, and orgasmic dysfunction.

7. The method of claim 6, wherein the mammal is human.

8. The method of claim 7, comprising administering the heptapeptide intranasally for at least 10 days.

9. The method of claim 7, comprising administering the heptapeptide intranasally for at least 15 days.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: synthetic peptide
```

```
<400> SEQUENCE: 1

Thr Lys Pro Arg Pro Gly Pro
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Cys Tyr Ile Gln Asn Cys Pro Leu Gly
 1               5
```